US008442608B2

(12) United States Patent
Pav

(10) Patent No.: US 8,442,608 B2
(45) Date of Patent: May 14, 2013

(54) SYSTEM AND METHOD FOR ESTIMATING PHYSIOLOGICAL PARAMETERS BY DECONVOLVING ARTIFACTS

(75) Inventor: Steven E. Pav, San Francisco, CA (US)

(73) Assignee: Covidien LP, Mansfield, MA (US)

(*) Notice: Subject to any disclaimer, the term of this patent is extended or adjusted under 35 U.S.C. 154(b) by 1172 days.

(21) Appl. No.: 12/343,838

(22) Filed: Dec. 24, 2008

(65) Prior Publication Data

US 2009/0187085 A1 Jul. 23, 2009

Related U.S. Application Data

(60) Provisional application No. 61/009,399, filed on Dec. 28, 2007.

(51) Int. Cl.
*A61B 5/1455* (2006.01)

(52) U.S. Cl.
USPC ............ 600/336; 600/310; 600/322; 600/323

(58) Field of Classification Search .................. 600/310, 600/322, 323, 330, 331, 473, 476, 336; 702/191
See application file for complete search history.

(56) References Cited

U.S. PATENT DOCUMENTS

| 3,721,813 | A |   | 3/1973  | Condon et al. |
|-----------|---|---|---------|---------------|
| 4,289,141 | A |   | 9/1981  | Cormier       |
| 4,407,290 | A | * | 10/1983 | Wilber ............................ 600/330 |
| 4,586,513 | A |   | 5/1986  | Hamaguri      |
| 4,603,700 | A |   | 8/1986  | Nichols et al. |
| 4,621,643 | A |   | 11/1986 | New, Jr. et al. |
| 4,653,498 | A |   | 3/1987  | New, Jr. et al. |
| 4,685,464 | A |   | 8/1987  | Goldberger et al. |
| 4,694,833 | A |   | 9/1987  | Hamaguri |
| 4,697,593 | A |   | 10/1987 | Evans et al. |
| 4,700,708 | A |   | 10/1987 | New, Jr. et al. |
| 4,714,080 | A |   | 12/1987 | Edgar, Jr. et al. |
| 4,714,341 | A |   | 12/1987 | Hamaguri et al. |
| 4,759,369 | A |   | 7/1988  | Taylor |
| 4,770,179 | A |   | 9/1988  | New, Jr. et al. |
| 4,773,422 | A |   | 9/1988  | Isaacson et al. |
| 4,776,339 | A |   | 10/1988 | Schreiber |
| 4,781,195 | A |   | 11/1988 | Martin |
| 4,796,636 | A |   | 1/1989  | Branstetter et al. |
| 4,800,495 | A |   | 1/1989  | Smith |

(Continued)

FOREIGN PATENT DOCUMENTS

| EP | 1491135 | 12/2004 |
|----|---------|---------|
| JP | 6154177 | 6/1994  |

(Continued)

OTHER PUBLICATIONS

Smith, "The scientist and Engineer's Guide to Digital Signal Processing" (retrieved from http://www.dspguide.com/ch17/2.htm.*

(Continued)

*Primary Examiner* — Eric Winakur
*Assistant Examiner* — Chu Chuan Liu

(57) ABSTRACT

There is disclosed a system and methods to estimate physiological parameters. In accordance with embodiments a method is disclosed which includes generating distribution data for a plurality of signals. The method may also include deconvolving one of the plurality of signals from the other plurality of signals to produce clean signals. The clean signals may then be used to calculate physiological parameters.

22 Claims, 7 Drawing Sheets

U.S. PATENT DOCUMENTS

| | | | |
|---|---|---|---|
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hansmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,972,331 A | 11/1990 | Chance | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A | 7/1991 | Muz | |
| 5,040,539 A | 8/1991 | Schmitt et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H1039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| 5,119,815 A | 6/1992 | Chance | |
| 5,122,974 A | 6/1992 | Chance | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,185,805 A * | 2/1993 | Chiang | 381/59 |
| 5,188,108 A | 2/1993 | Secker | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp, Jr. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Freidman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,273,036 A | 12/1993 | Kronberg et al. | |
| 5,275,159 A | 1/1994 | Griebel | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Freidman et al. | |
| 5,311,865 A | 5/1994 | Mayeux | |
| 5,313,940 A | 5/1994 | Fuse et al. | |
| 5,323,776 A | 6/1994 | Blakeley et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |
| 5,385,143 A | 1/1995 | Aoyagi | |
| 5,386,827 A | 2/1995 | Chance et al. | |
| 5,387,122 A | 2/1995 | Goldberger et al. | |
| 5,390,670 A | 2/1995 | Centa et al. | |
| 5,392,777 A | 2/1995 | Swedlow et al. | |
| 5,398,680 A | 3/1995 | Polson et al. | |
| 5,402,777 A | 4/1995 | Warring et al. | |
| 5,402,778 A | 4/1995 | Chance | |
| 5,411,023 A | 5/1995 | Morris, Sr. et al. | |
| 5,411,024 A | 5/1995 | Thomas et al. | |
| 5,413,099 A | 5/1995 | Schmidt et al. | |
| 5,413,100 A | 5/1995 | Barthelemy et al. | |
| 5,413,101 A | 5/1995 | Sugiura | |
| 5,413,102 A | 5/1995 | Schmidt et al. | |

| Patent | Date | Inventor |
|---|---|---|
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,555,885 A | 9/1996 | Chance |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |

| | | | | | | |
|---|---|---|---|---|---|---|
| 5,902,235 A | 5/1999 | Lewis et al. | | 6,150,951 A | 11/2000 | Olejniczak |
| 5,910,108 A | 6/1999 | Solenberger | | 6,151,107 A | 11/2000 | Schöllermann et al. |
| 5,911,690 A | 6/1999 | Rall | | 6,151,518 A | 11/2000 | Hayashi |
| 5,912,656 A | 6/1999 | Tham et al. | | 6,152,754 A | 11/2000 | Gerhardt et al. |
| 5,913,819 A | 6/1999 | Taylor et al. | | 6,154,667 A | 11/2000 | Miura et al. |
| 5,916,154 A | 6/1999 | Hobbs et al. | | 6,157,850 A | 12/2000 | Diab et al. |
| 5,916,155 A | 6/1999 | Levinson et al. | | 6,163,715 A | 12/2000 | Larsen et al. |
| 5,919,133 A | 7/1999 | Taylor et al. | | 6,165,005 A | 12/2000 | Mills et al. |
| 5,919,134 A | 7/1999 | Diab | | 6,173,196 B1 | 1/2001 | Delonzor et al. |
| 5,920,263 A | 7/1999 | Huttenhoff et al. | | 6,178,343 B1 | 1/2001 | Bindszus et al. |
| 5,921,921 A | 7/1999 | Potratz et al. | | 6,181,958 B1 | 1/2001 | Steuer et al. |
| 5,922,607 A | 7/1999 | Bernreuter | | 6,181,959 B1 | 1/2001 | Schöllermann et al. |
| 5,924,979 A | 7/1999 | Swedlow et al. | | 6,184,521 B1 | 2/2001 | Coffin, IV et al. |
| 5,924,980 A | 7/1999 | Coetzee | | 6,188,470 B1 | 2/2001 | Grace |
| 5,924,982 A | 7/1999 | Chin | | 6,192,260 B1 | 2/2001 | Chance |
| 5,924,985 A | 7/1999 | Jones | | 6,195,575 B1 | 2/2001 | Levinson |
| 5,934,277 A | 8/1999 | Mortz | | 6,198,951 B1 | 3/2001 | Kosuda et al. |
| 5,934,925 A | 8/1999 | Tobler et al. | | 6,206,830 B1 | 3/2001 | Diab et al. |
| 5,940,182 A | 8/1999 | Lepper, Jr. et al. | | 6,213,952 B1 | 4/2001 | Finarov et al. |
| 5,954,644 A | 9/1999 | Dettling et al. | | 6,217,523 B1 | 4/2001 | Amano et al. |
| 5,960,610 A | 10/1999 | Levinson et al. | | 6,222,189 B1 | 4/2001 | Misner et al. |
| 5,961,450 A | 10/1999 | Merchant et al. | | 6,226,539 B1 | 5/2001 | Potratz |
| 5,961,452 A | 10/1999 | Chung et al. | | 6,226,540 B1 | 5/2001 | Bernreuter |
| 5,964,701 A | 10/1999 | Asada et al. | | 6,229,856 B1 | 5/2001 | Diab et al. |
| 5,971,930 A | 10/1999 | Elghazzawi | | 6,230,035 B1 | 5/2001 | Aoyagi et al. |
| 5,978,691 A | 11/1999 | Mills | | 6,233,470 B1 | 5/2001 | Tsuchiya |
| 5,978,693 A | 11/1999 | Hamilton et al. | | 6,236,871 B1 | 5/2001 | Tsuchiya |
| 5,983,122 A | 11/1999 | Jarman et al. | | 6,236,872 B1 | 5/2001 | Diab et al. |
| 5,987,343 A | 11/1999 | Kinast | | 6,240,305 B1 | 5/2001 | Tsuchiya |
| 5,991,648 A | 11/1999 | Levin | | 6,253,097 B1 | 6/2001 | Aronow et al. |
| 5,995,855 A | 11/1999 | Kiani et al. | | 6,253,098 B1 | 6/2001 | Walker et al. |
| 5,995,856 A | 11/1999 | Mannheimer et al. | | 6,256,523 B1 | 7/2001 | Diab et al. |
| 5,995,858 A | 11/1999 | Kinast | | 6,256,524 B1 | 7/2001 | Walker et al. |
| 5,995,859 A | 11/1999 | Takahashi | | 6,261,236 B1 | 7/2001 | Grimblatov |
| 5,997,343 A | 12/1999 | Mills et al. | | 6,263,221 B1 | 7/2001 | Chance et al. |
| 5,999,834 A | 12/1999 | Wang et al. | | 6,263,222 B1 | 7/2001 | Diab et al. |
| 6,002,952 A | 12/1999 | Diab et al. | | 6,263,223 B1 | 7/2001 | Sheperd et al. |
| 6,005,658 A | 12/1999 | Kaluza et al. | | 6,266,546 B1 | 7/2001 | Steuer et al. |
| 6,006,120 A | 12/1999 | Levin | | 6,266,547 B1 | 7/2001 | Walker et al. |
| 6,011,985 A | 1/2000 | Athan et al. | | 6,272,363 B1 | 8/2001 | Casciani et al. |
| 6,011,986 A | 1/2000 | Diab et al. | | 6,278,522 B1 | 8/2001 | Lepper, Jr. et al. |
| 6,014,576 A | 1/2000 | Raley et al. | | 6,280,213 B1 | 8/2001 | Tobler et al. |
| 6,018,673 A | 1/2000 | Chin et al. | | 6,280,381 B1 | 8/2001 | Malin et al. |
| 6,018,674 A | 1/2000 | Aronow | | 6,285,894 B1 | 9/2001 | Oppelt et al. |
| 6,022,321 A | 2/2000 | Amano et al. | | 6,285,895 B1 | 9/2001 | Ristolainen et al. |
| 6,023,541 A | 2/2000 | Merchant et al. | | 6,285,896 B1 | 9/2001 | Tobler et al. |
| 6,026,312 A | 2/2000 | Shemwell et al. | | 6,298,252 B1 | 10/2001 | Kovach et al. |
| 6,026,314 A | 2/2000 | Amerov et al. | | 6,308,089 B1 | 10/2001 | Von der Ruhr et al. |
| 6,031,603 A | 2/2000 | Fine et al. | | 6,321,100 B1 | 11/2001 | Parker |
| 6,035,223 A | 3/2000 | Baker, Jr. | | 6,330,468 B1 | 12/2001 | Scharf |
| 6,036,642 A | 3/2000 | Diab et al. | | 6,334,065 B1 | 12/2001 | Al-Ali et al. |
| 6,041,247 A | 3/2000 | Weckstrom et al. | | 6,339,715 B1 | 1/2002 | Bahr et al. |
| 6,044,283 A | 3/2000 | Fein et al. | | 6,343,223 B1 | 1/2002 | Chin et al. |
| 6,047,201 A | 4/2000 | Jackson, III | | 6,343,224 B1 | 1/2002 | Parker |
| 6,061,584 A | 5/2000 | Lovejoy et al. | | 6,349,228 B1 | 2/2002 | Kiani et al. |
| 6,064,898 A | 5/2000 | Aldrich | | 6,351,658 B1 | 2/2002 | Middleman et al. |
| 6,064,899 A | 5/2000 | Fein et al. | | 6,353,750 B1 | 3/2002 | Kimura et al. |
| 6,067,462 A | 5/2000 | Diab et al. | | 6,356,774 B1 | 3/2002 | Bernstein et al. |
| 6,073,038 A | 6/2000 | Wang et al. | | 6,360,113 B1 | 3/2002 | Dettling |
| 6,075,610 A | 6/2000 | Ueda et al. | | 6,360,114 B1 | 3/2002 | Diab et al. |
| 6,078,833 A | 6/2000 | Hueber | | 6,361,501 B1 | 3/2002 | Amano et al. |
| 6,081,735 A | 6/2000 | Diab et al. | | 6,363,269 B1 | 3/2002 | Hanna et al. |
| 6,081,742 A | 6/2000 | Amano et al. | | 6,370,408 B1 | 4/2002 | Merchant et al. |
| 6,083,157 A | 7/2000 | Noller | | 6,370,409 B1 | 4/2002 | Chung et al. |
| 6,083,172 A | 7/2000 | Baker, Jr. et al. | | 6,374,129 B1 | 4/2002 | Chin et al. |
| 6,088,607 A | 7/2000 | Diab et al. | | 6,377,829 B1 | 4/2002 | Al-Ali et al. |
| 6,094,592 A | 7/2000 | Yorkey et al. | | 6,381,479 B1 | 4/2002 | Norris |
| 6,095,974 A | 8/2000 | Shemwell et al. | | 6,381,480 B1 | 4/2002 | Stoddar et al. |
| 6,104,938 A | 8/2000 | Huiku et al. | | 6,385,471 B1 | 5/2002 | Mortz |
| 6,112,107 A | 8/2000 | Hannula | | 6,385,821 B1 | 5/2002 | Modgil et al. |
| 6,113,541 A | 9/2000 | Dias et al. | | 6,388,240 B2 | 5/2002 | Schulz et al. |
| 6,115,621 A | 9/2000 | Chin | | 6,393,310 B1 | 5/2002 | Kuenster |
| 6,122,535 A | 9/2000 | Kaestle et al. | | 6,397,091 B2 | 5/2002 | Diab et al. |
| 6,133,994 A | 10/2000 | Mathews et al. | | 6,397,092 B1 | 5/2002 | Norris et al. |
| 6,135,952 A | 10/2000 | Coetzee | | 6,397,093 B1 | 5/2002 | Aldrich |
| 6,144,444 A | 11/2000 | Haworth et al. | | 6,400,971 B1 | 6/2002 | Finarov et al. |
| 6,144,867 A | 11/2000 | Walker et al. | | 6,400,972 B1 | 6/2002 | Fine |
| 6,144,868 A | 11/2000 | Parker | | 6,402,690 B1 | 6/2002 | Rhee et al. |
| 6,149,481 A | 11/2000 | Wang et al. | | 6,405,069 B1 | 6/2002 | Oraevsky et al. |

| | | | | | | |
|---|---|---|---|---|---|---|
| 6,408,198 B1 | 6/2002 | Hanna et al. | | 6,650,917 B2 | 11/2003 | Diab et al. |
| 6,411,832 B1 | 6/2002 | Guthermann | | 6,650,918 B2 | 11/2003 | Terry |
| 6,411,833 B1 | 6/2002 | Baker, Jr. et al. | | 6,654,621 B2 | 11/2003 | Palatnik et al. |
| 6,419,671 B1 | 7/2002 | Lemberg | | 6,654,622 B1 | 11/2003 | Eberhard et al. |
| 6,421,549 B1 | 7/2002 | Jacques | | 6,654,623 B1 | 11/2003 | Kästle |
| 6,430,423 B2 | 8/2002 | DeLonzor et al. | | 6,654,624 B2 | 11/2003 | Diab et al. |
| 6,430,513 B1 | 8/2002 | Wang et al. | | 6,658,276 B2 | 12/2003 | Kianl et al. |
| 6,430,525 B1 | 8/2002 | Weber et al. | | 6,658,277 B2 | 12/2003 | Wasserman |
| 6,434,408 B1 | 8/2002 | Heckel | | 6,662,033 B2 | 12/2003 | Casciani et al. |
| 6,438,399 B1 | 8/2002 | Kurth | | 6,665,551 B1 | 12/2003 | Suzuki |
| 6,449,501 B1 | 9/2002 | Reuss | | 6,668,182 B2 | 12/2003 | Hubelbank |
| 6,453,183 B1 | 9/2002 | Walker | | 6,668,183 B2 | 12/2003 | Hicks et al. |
| 6,453,184 B1 | 9/2002 | Hyogo et al. | | 6,671,526 B1 | 12/2003 | Aoyagi et al. |
| 6,456,862 B2 | 9/2002 | Benni | | 6,671,528 B2 | 12/2003 | Steuer et al. |
| 6,461,305 B1 | 10/2002 | Schnall | | 6,671,530 B2 | 12/2003 | Chung et al. |
| 6,463,310 B1 | 10/2002 | Swedlow et al. | | 6,671,531 B2 | 12/2003 | Al-Ali et al. |
| 6,463,311 B1 | 10/2002 | Diab | | 6,671,532 B1 | 12/2003 | Fudge et al. |
| 6,466,808 B1 | 10/2002 | Chin et al. | | 6,675,031 B1 | 1/2004 | Porges et al. |
| 6,466,809 B1 | 10/2002 | Riley | | 6,678,543 B2 | 1/2004 | Diab et al. |
| 6,470,199 B1 | 10/2002 | Kopotic et al. | | 6,681,126 B2 | 1/2004 | Solenberger |
| 6,470,200 B2 | 10/2002 | Walker et al. | | 6,681,128 B2 | 1/2004 | Steuer et al. |
| 6,480,729 B2 | 11/2002 | Stone | | 6,681,454 B2 | 1/2004 | Modgil et al. |
| 6,490,466 B1 | 12/2002 | Fein et al. | | 6,684,090 B2 | 1/2004 | Ali et al. |
| 6,496,711 B1 | 12/2002 | Athan et al. | | 6,684,091 B2 | 1/2004 | Parker |
| 6,498,942 B1 | 12/2002 | Esenaliev et al. | | 6,694,160 B2 | 2/2004 | Chin |
| 6,501,974 B2 | 12/2002 | Huiku | | 6,697,653 B2 | 2/2004 | Hanna |
| 6,501,975 B2 | 12/2002 | Diab et al. | | 6,697,655 B2 | 2/2004 | Sueppel et al. |
| 6,505,060 B1 | 1/2003 | Norris | | 6,697,656 B1 | 2/2004 | Al-Ali |
| 6,505,061 B2 | 1/2003 | Larson | | 6,697,658 B2 | 2/2004 | Al-Ali |
| 6,505,133 B1 | 1/2003 | Hanna et al. | | RE38,476 E | 3/2004 | Diab et al. |
| 6,510,329 B2 | 1/2003 | Heckel | | 6,699,194 B1 | 3/2004 | Diab et al. |
| 6,510,331 B1 | 1/2003 | Williams et al. | | 6,699,199 B2 | 3/2004 | Asada et al. |
| 6,512,937 B2 | 1/2003 | Blank et al. | | 6,701,170 B2 | 3/2004 | Stetson |
| 6,515,273 B2 | 2/2003 | Al-Ali | | 6,702,752 B2 | 3/2004 | Dekker |
| 6,519,484 B1 | 2/2003 | Lovejoy et al. | | 6,707,257 B2 | 3/2004 | Norris |
| 6,519,486 B1 | 2/2003 | Edgar, Jr. et al. | | 6,708,049 B1 | 3/2004 | Berson et al. |
| 6,519,487 B1 | 2/2003 | Parker | | 6,709,402 B2 | 3/2004 | Dekker |
| 6,525,386 B1 | 2/2003 | Mills et al. | | 6,711,424 B1 | 3/2004 | Fine et al. |
| 6,526,300 B1 | 2/2003 | Kiani et al. | | 6,711,425 B1 | 3/2004 | Reuss |
| 6,526,301 B2 | 2/2003 | Larsen et al. | | 6,714,803 B1 | 3/2004 | Mortz |
| 6,541,756 B2 | 4/2003 | Schulz et al. | | 6,714,804 B2 | 3/2004 | Al-Ali et al. |
| 6,542,764 B1 | 4/2003 | Al-Ali et al. | | 6,714,805 B2 | 3/2004 | Jeon et al. |
| 6,546,267 B1 | 4/2003 | Sugiura et al. | | RE38,492 E | 4/2004 | Diab et al. |
| 6,553,241 B2 | 4/2003 | Mannheimer et al. | | 6,719,686 B2 | 4/2004 | Coakley et al. |
| 6,553,242 B1 | 4/2003 | Sarussi | | 6,719,705 B2 | 4/2004 | Mills |
| 6,553,243 B2 | 4/2003 | Gurley | | 6,720,734 B2 | 4/2004 | Norris |
| 6,556,852 B1 | 4/2003 | Schulze et al. | | 6,721,584 B2 | 4/2004 | Baker, Jr. et al. |
| 6,560,470 B1 | 5/2003 | Pologe | | 6,721,585 B1 | 4/2004 | Parker |
| 6,564,077 B2 | 5/2003 | Mortara | | 6,725,074 B1 | 4/2004 | Kästle |
| 6,564,088 B1 | 5/2003 | Soller et al. | | 6,725,075 B2 | 4/2004 | Al-Ali |
| 6,571,113 B1 | 5/2003 | Fein et al. | | 6,731,963 B2 | 5/2004 | Finarov et al. |
| 6,571,114 B1 | 5/2003 | Koike et al. | | 6,731,967 B1 | 5/2004 | Turcott |
| 6,574,491 B2 | 6/2003 | Elghazzawi | | 6,735,459 B2 | 5/2004 | Parker |
| 6,580,086 B1 | 6/2003 | Schulz et al. | | 6,745,060 B2 | 6/2004 | Diab et al. |
| 6,584,336 B1 | 6/2003 | Ali et al. | | 6,745,061 B1 | 6/2004 | Hicks et al. |
| 6,587,703 B2 | 7/2003 | Cheng et al. | | 6,748,253 B2 | 6/2004 | Norris et al. |
| 6,587,704 B1 | 7/2003 | Fine et al. | | 6,748,254 B2 | 6/2004 | Chin et al. |
| 6,589,172 B2 | 7/2003 | Williams et al. | | 6,754,515 B1 | 6/2004 | Pologe |
| 6,591,122 B2 | 7/2003 | Schmitt | | 6,754,516 B2 | 6/2004 | Mannheimer |
| 6,591,123 B2 | 7/2003 | Fein et al. | | 6,760,607 B2 | 7/2004 | Al-Ali |
| 6,594,511 B2 | 7/2003 | Stone et al. | | 6,760,609 B2 | 7/2004 | Jacques |
| 6,594,512 B2 | 7/2003 | Huang | | 6,760,610 B2 | 7/2004 | Tscupp et al. |
| 6,594,513 B1 | 7/2003 | Jobsis et al. | | 6,763,255 B2 | 7/2004 | DeLonzor et al. |
| 6,597,931 B1 | 7/2003 | Cheng et al. | | 6,763,256 B2 | 7/2004 | Kimball et al. |
| 6,597,933 B2 | 7/2003 | Kiani et al. | | 6,770,028 B1 | 8/2004 | Ali et al. |
| 6,600,940 B1 | 7/2003 | Fein et al. | | 6,771,994 B2 | 8/2004 | Kiani et al. |
| 6,606,510 B2 | 8/2003 | Swedlow et al. | | 6,773,397 B2 | 8/2004 | Kelly |
| 6,606,511 B1 | 8/2003 | Ali et al. | | 6,778,923 B2 | 8/2004 | Norris et al. |
| 6,606,512 B2 | 8/2003 | Muz et al. | | 6,780,158 B2 | 8/2004 | Yarita |
| 6,615,064 B1 | 9/2003 | Aldrich | | 6,791,689 B1 | 9/2004 | Weckström |
| 6,615,065 B1 | 9/2003 | Barrett et al. | | 6,792,300 B1 | 9/2004 | Diab et al. |
| 6,618,602 B2 | 9/2003 | Levin et al. | | 6,793,654 B2 | 9/2004 | Lemberg |
| 6,622,034 B1 | 9/2003 | Gorski et al. | | 6,801,797 B2 | 10/2004 | Mannheimer et al. |
| 6,628,975 B1 | 9/2003 | Fein et al. | | 6,801,798 B2 | 10/2004 | Geddes et al. |
| 6,631,281 B1 | 10/2003 | Kästle | | 6,801,799 B2 | 10/2004 | Mendelson |
| 6,643,530 B2 | 11/2003 | Diab et al. | | 6,801,802 B2 | 10/2004 | Sitzman et al. |
| 6,643,531 B1 | 11/2003 | Katarow | | 6,802,812 B1 | 10/2004 | Walker et al. |
| 6,647,279 B2 | 11/2003 | Pologe | | 6,805,673 B2 | 10/2004 | Dekker |
| 6,647,280 B2 | 11/2003 | Bahr et al. | | 6,810,277 B2 | 10/2004 | Edgar, Jr. et al. |

| | | | |
|---|---|---|---|
| 6,813,511 B2 | 11/2004 | Diab et al. | |
| 6,816,741 B2 | 11/2004 | Diab | |
| 6,819,950 B2 | 11/2004 | Mills | |
| 6,822,564 B2 | 11/2004 | Al-Ali | |
| 6,825,619 B2 | 11/2004 | Norris | |
| 6,826,419 B2 | 11/2004 | Diab et al. | |
| 6,829,496 B2 | 12/2004 | Nagai et al. | |
| 6,830,711 B2 | 12/2004 | Mills et al. | |
| 6,836,679 B2 | 12/2004 | Baker, Jr. et al. | |
| 6,839,579 B1 | 1/2005 | Chin | |
| 6,839,580 B2 | 1/2005 | Zonios et al. | |
| 6,839,582 B2 | 1/2005 | Heckel | |
| 6,839,659 B2 | 1/2005 | Tarassenko et al. | |
| 6,842,635 B1 | 1/2005 | Parker | |
| 6,845,256 B2 | 1/2005 | Chin et al. | |
| 6,850,787 B2 | 2/2005 | Weber et al. | |
| 6,850,788 B2 | 2/2005 | Al-Ali | |
| 6,850,789 B2 | 2/2005 | Schweitzer, Jr. et al. | |
| 6,861,639 B2 | 3/2005 | Al-Ali | |
| 6,863,652 B2 | 3/2005 | Huang et al. | |
| 6,865,407 B2 | 3/2005 | Kimball et al. | |
| 6,879,850 B2 | 4/2005 | Kimball | |
| 6,882,874 B2 | 4/2005 | Huiku | |
| 6,889,153 B2 | 5/2005 | Dietiker | |
| 6,898,452 B2 | 5/2005 | Al-Ali et al. | |
| 6,909,912 B2 | 6/2005 | Melker | |
| 6,912,413 B2 | 6/2005 | Rantala et al. | |
| 6,916,289 B2 | 7/2005 | Schnall | |
| 6,920,345 B2 | 7/2005 | Al-Ali et al. | |
| 6,931,269 B2 | 8/2005 | Terry | |
| 6,934,570 B2 | 8/2005 | Kiani et al. | |
| 6,939,307 B1 | 9/2005 | Dunlop | |
| 6,941,162 B2 | 9/2005 | Fudge et al. | |
| 6,947,781 B2 | 9/2005 | Asada et al. | |
| 6,950,687 B2 | 9/2005 | Al-Ali | |
| 6,963,767 B2 | 11/2005 | Rantala et al. | |
| 6,971,580 B2 | 12/2005 | DeLonzor et al. | |
| 6,983,178 B2 | 1/2006 | Fine et al. | |
| 6,985,763 B2 | 1/2006 | Boas et al. | |
| 6,985,764 B2 | 1/2006 | Mason et al. | |
| 6,990,426 B2 | 1/2006 | Yoon et al. | |
| 6,992,751 B2 | 1/2006 | Al-Ali | |
| 6,992,772 B2 | 1/2006 | Block et al. | |
| 6,993,371 B2 | 1/2006 | Kiani et al. | |
| 6,993,372 B2 | 1/2006 | Fine et al. | |
| 6,996,427 B2 | 2/2006 | Ali et al. | |
| 7,003,338 B2 | 2/2006 | Weber et al. | |
| 7,003,339 B2 | 2/2006 | Diab et al. | |
| 7,006,855 B1 | 2/2006 | Sarussi | |
| 7,006,856 B2 | 2/2006 | Baker, Jr. et al. | |
| 7,016,715 B2 | 3/2006 | Stetson | |
| 7,020,507 B2 | 3/2006 | Scharf et al. | |
| 7,024,233 B2 | 4/2006 | Ali et al. | |
| 7,024,235 B2 | 4/2006 | Melker et al. | |
| 7,025,728 B2 | 4/2006 | Ito et al. | |
| 7,027,849 B2 | 4/2006 | Al-Ali et al. | |
| 7,027,850 B2 | 4/2006 | Wasserman | |
| 7,035,697 B1 | 4/2006 | Brown | |
| 7,039,449 B2 | 5/2006 | Al-Ali | |
| 7,043,289 B2 | 5/2006 | Fine et al. | |
| 7,047,055 B2 | 5/2006 | Boaz et al. | |
| 7,047,056 B2 | 5/2006 | Hannula et al. | |
| 7,060,035 B2 | 6/2006 | Wasserman | |
| 7,062,307 B2 | 6/2006 | Norris et al. | |
| 7,067,893 B2 | 6/2006 | Mills et al. | |
| 7,072,701 B2 | 7/2006 | Chen et al. | |
| 7,072,702 B2 | 7/2006 | Edgar, Jr. et al. | |
| 7,079,880 B2 | 7/2006 | Stetson | |
| 7,085,597 B2 | 8/2006 | Fein et al. | |
| 7,096,052 B2 | 8/2006 | Mason et al. | |
| 7,096,054 B2 | 8/2006 | Abdul-Hafiz et al. | |
| 7,107,088 B2 | 9/2006 | Aceti | |
| 7,113,815 B2 | 9/2006 | O'Neil et al. | |
| 7,123,950 B2 | 10/2006 | Mannheimer | |
| 7,127,278 B2 | 10/2006 | Melker et al. | |
| 7,130,671 B2 | 10/2006 | Baker, Jr. et al. | |
| 7,132,641 B2 | 11/2006 | Schulz et al. | |
| 7,133,711 B2 | 11/2006 | Chernoguz et al. | |
| 7,139,559 B2 | 11/2006 | Terry | |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,218,959 B2 | 5/2007 | Alfano et al. |
| 7,225,006 B2 | 5/2007 | Al-Ali et al. |
| 7,236,811 B2 | 6/2007 | Schmitt |
| 7,236,881 B2 | 6/2007 | Schmitt |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Schmid |
| 7,280,858 B2 | 10/2007 | Al-Ali et al. |
| 7,289,835 B2 | 10/2007 | Mansfield et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |

| | | |
|---|---|---|
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0113651 A1 | 5/2005 | Wood et al. |
| 2005/0177034 A1 | 8/2005 | Beaumont |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0122476 A1 | 6/2006 | Van Slyke |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2006/0276700 A1 | 12/2006 | O'Neil |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |

FOREIGN PATENT DOCUMENTS

| | | |
|---|---|---|
| JP | 7136150 | 5/1995 |
| JP | 2003194714 | 7/2003 |
| JP | 2003210438 | 7/2003 |
| JP | 2004248819 | 9/2004 |
| WO | WO9101678 | 2/1991 |
| WO | WO9309711 | 5/1993 |
| WO | WO9423643 | 10/1994 |

OTHER PUBLICATIONS

Such, Hans Olaf; "Optoelectronic Non-invasive Vascular Diagnostics Using multiple Wavelength and Imaging Approach," *Dissertation*, (1998).

Cysewska-Sobusaik, Anna; "Metrological Problems With noninvasive Transillumination of Living Tissues," *Proceedings of SPIE*, vol. 4515, pp. 15-24 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

* cited by examiner

SYSTEM AND METHOD FOR ESTIMATING PHYSIOLOGICAL PARAMETERS BY DECONVOLVING ARTIFACTS

RELATED APPLICATIONS

This application claims priority to U.S. Provisional Application No. 61/009,399, filed Dec. 28, 2007, and is incorporated herein by reference in its entirety.

BACKGROUND

The present disclosure relates generally to medical devices and, more particularly, to non-invasive medical devices and methods used for determining physiological parameters.

This section is intended to introduce the reader to various aspects that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices may have been developed for monitoring many such characteristics of a patient. Such devices may provide doctors and other healthcare personnel with the information they need to provide the best possible healthcare for their patients. As a result, such monitoring devices have become useful in treating patients.

Non-invasive medical devices may be particularly useful and desirable, as they generally provide immediate feedback and do not traumatize a patient. Generally, non-invasive sensors may transmit electromagnetic radiation, such as light, through a patient's tissue. The sensor may photoelectrically detect the absorption and scattering of the transmitted light in such tissue. The light passed through the tissue may be selected to be of one or more wavelengths that may be absorbed and scattered by particular tissue constituents, such as blood, for example. One or more physiological characteristics may then be calculated based upon the amount of light absorbed and/or scattered.

One non-invasive technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximetry readings may measure the pulsatile, dynamic changes in amount and type of blood constituents in tissue. However, events other than the pulsing of arterial blood, such as noise received by the sensor, for example, may lead to modulation of the light path, direction, and the amount of light detected by the sensor, introducing error to the measurements. As such, various types of noise are primary causes of artifacts that may obscure determination of the blood constituent signal and make it difficult to obtain accurate measurements.

SUMMARY

Certain aspects commensurate in scope with the disclosure are set forth below. It should be understood that these aspects are presented merely to provide the reader with a brief summary of certain forms the embodiments might take and, these aspects are not intended to limit the scope of the disclosure. Indeed, the disclosure may encompass a variety of aspects that may not be set forth below.

In an embodiment, there is provided a method for non-invasively estimating physiological parameters. The method may include detecting light from a plurality of light sources and generating respective distributions for the detected light of each of the plurality of light sources. The distribution for the detected light of one of the plurality of light sources may be deconvolved from each of the other distributions for the detected light from the other plurality of light sources to produce clean distributions. Physiological parameters may then be estimated using the clean distributions.

In an embodiment, there is provided a system for estimating the physiological parameters. The system may include a sensor comprising a plurality of light sources and a detector configured to generate signals based on light detected from the plurality of light sources. The system also includes a monitor coupled to the sensor. The monitor may be configured to generate distribution data for each of the plurality of light sources and deconvolve distribution data of one of the plurality of light sources from the distribution data of each of the other plurality of light sources.

In an embodiment, there is provided a method of calibration. The method of calibration may include collecting data during two time intervals and generating normalized density estimators representing the data collected during the two time intervals. The calibration method may also include finding a transform function such that the equality $f_2 * h_1 = f_1 * h_2$ is true, wherein $f_1$ is a vector representing data collected during the first time interval, $f_2$ is a vector representing data collected during the second time interval, $h_1$ is a density estimator representing the data from the first time interval, $h_2$ is a density estimator representing data from the second time interval, and "*" is the convolution operator.

BRIEF DESCRIPTION OF THE DRAWINGS

Advantages of embodiments may become apparent upon reading the following detailed description and upon reference to the drawings in which.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present disclosure, a system and method are disclosed for estimating physiological parameters after deconvolving artifacts. In particular, in accordance with an embodiment, techniques for estimating percent oxygen saturation are disclosed using a third channel to estimate the distribution of noise. Specifically, distributions for an IR spectrum and a red spectrum may be generated after they have passed through blood perfused tissue. An estimated artifact distribution may be obtained using a third wavelength. In an embodiment, the estimated artifact distribution may be deconvolved from the distributions for the IR and red signals, thus, cleaning artifacts from the IR and red distributions. In an embodiment, once the artifact distribution is deconvolved from the IR and the red signals, the ratio-of-ratios, or "ratrat", can be calculated to determine the percent saturation of oxygen in hemoglobin.

Using the present techniques, the distribution of the artifacts may be estimated and not the artifact signal itself. Additionally, the clean IR and red signals may not be de-noised signals, rather a de-noised distribution. As such, consistent saturation readings may be provided even in situations providing highly artifacted signals, and the system and methods disclosed herein may be useful to provide distributions to a maximum likelihood saturation estimator.

Figure 1:
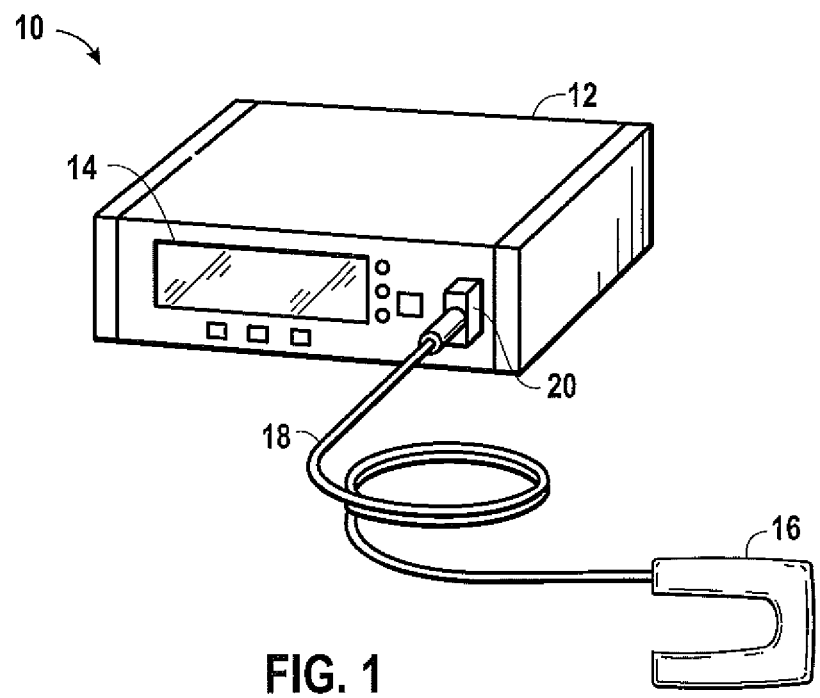
FIG. 1 illustrates a pulse oximeter in accordance with an embodiment.

Referring to the figures and turning initially to FIG. 1, a pulse oximeter system is illustrated in accordance with an embodiment and is generally designated by the reference numeral 10. In an embodiment, the system 10 includes a monitor 12 which may house hardware and software configured to compute various physiological parameters. The monitor 12 may include a display 14 to display the various physiological parameters. For example, the display 14 may display the percent oxygen saturation of hemoglobin and the pulse rate.

Figure 2:
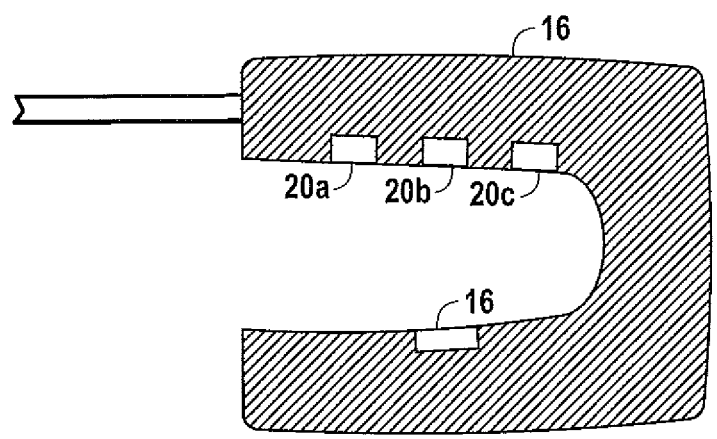
FIG. 2 illustrates a cross-sectional view of a pulse oximeter sensor in accordance with an embodiment.

In an embodiment, a sensor 16 may be communicatively coupled to the monitor 12 via a cable 18 and a connector 20. A cross-sectional view of the sensor 16 is illustrated in FIG. 2. As can be seen, the sensor 16 may have three emitters 20a-c capable of directing electromagnetic radiation, or light, toward a detector 22. In an embodiment, each emitter 20a-c may emit light at a unique wavelength.

In an embodiment, the first emitter 20a may emit light in the red region of the electromagnetic spectrum and the second emitter 20b may emit light in the infrared (IR) region of the electromagnetic spectrum. The third emitter 20c may emit light having a wavelength selected to maximize the detection of noise that is introduced to the sensor signal. In accordance with an embodiment, the third emitter 20c may operate at about 1250 nm to 1350 nm, for example. Alternatively, the third emitter 20c may operate in the blue region of the electromagnetic spectrum at approximately 450 nm to 550 nm, for example. In other words, the third wavelength may be in the IR, red, blue, or other regions of the electromagnetic spectrum depending upon the wavelength range that may be best suited to address the expected noise. Additionally, in an embodiment, a combination of more than one wavelength may be used to estimate the distribution of noise, as will be discussed in greater detail below.

Figure 3:
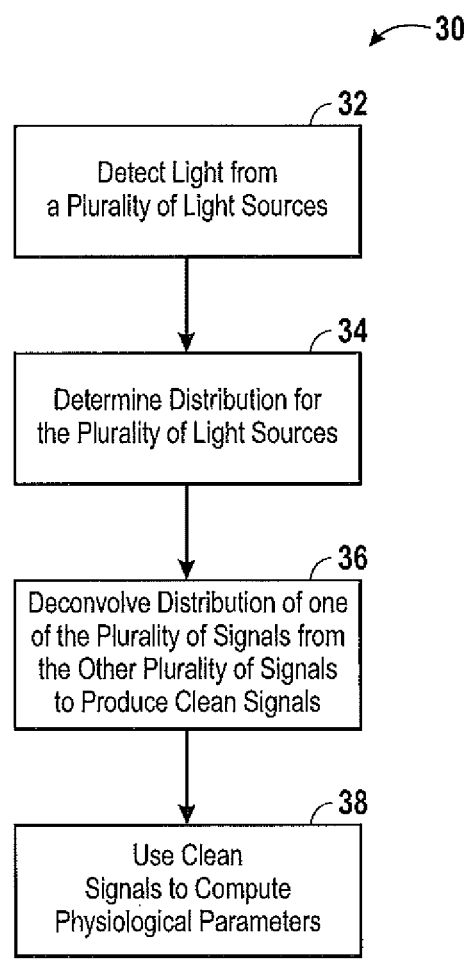
FIG. 3 is a flow chart illustrating an exemplary technique for estimating physiological parameters in accordance with an embodiment.

According to an embodiment, FIG. 3 illustrates a flow chart 30 for operating a non-invasive medical device, such as the pulse oximeter 10 shown in FIG. 1. In an embodiment, light from a plurality of light sources, i.e., the emitters 20a and 20b, is detected, as indicated at block 32. As discussed above, light from the emitters 20a-b passes through blood perfused tissue before being detected at the detector 22. The constituent parts of the blood perfused tissue reflect and absorb the light. In an embodiment, the detector 22 produces an electrical signal indicative of the light that arrives at the detector 22 which may be correlative to an optical density (OD) of the blood perfused tissue relative to the respective wavelengths. Generally, the optical density represents the absorbance of a material, in this case, blood perfused tissue. The electrical signal is transmitted to the monitor 12 for processing and calculation of physiological parameters.

In an embodiment, the optical density of the light emitted by emitters 20a-b, with respect to the pulse oximeter 10, detected at the detector 22, may be correlated to each other according to the equation:

$$v_k = s_k u_k, \quad (1)$$

where $v_k$ represents the optical density of a first signal, such as the red signal, for example, and $u_k$ represents the optical density for a second signal, such an IR signal, for example, at time k. The $s_k$ is the ratio of the two signals or ratrat at time k. The red and IR optical density signals may be scaled versions of underlying signals:

$$v_k = \alpha_k t_k, \text{ and} \quad (2)$$

$$u_k = \beta_k t_k, \quad (3)$$

where $t_k$ is e.g., the change in blood volume due to pulse. Thus, the ratrat is given by $s_k = \alpha_k/\beta_k$, and $\alpha_k$ and $\beta_k$ can be referred to as scale parameters or scales of the red and IR optical density signals, respectively.

The measurements of the red and IR optical density signals may be corrupted by non-signal artifact. As mentioned above, the non-signal artifacts may be induced by various types of noise received by the sensor. Because of the non-signal artifacts, in an embodiment, the measurements actually reflect:

$$v_k = \alpha_k t_k + \epsilon_k, \text{ and} \quad (4)$$

$$u_k = \beta_k t_k + \zeta_k, \quad (5)$$

where the variables $\epsilon_k$ and $\zeta_k$ are random noise artifacts. The relation of scales still holds, but equation 1 is replaced by:

$$v_k = s_k(u_k - \zeta_k) + \epsilon_k. \quad (6)$$

If $\epsilon_k$ and $\zeta_k$ are large compared to the signal values, then attempts to estimate the scale of the red and IR signals can fail. If $\epsilon_k$ and $\zeta_k$ are nearly equal and change over time with greater variation than the cardiac signal $t_k$, then the estimated scale parameters will converge to the same number, giving unity ratrat, or saturation nearly 80.

Therefore, in an embodiment, the scale parameters for the red and IR signals $\alpha_k$ and $\beta_k$ can be estimated accurately only if the influence of the random noise artifacts $\epsilon_k$ and $\zeta_k$ can be ignored. To do so, physical observations at wavelengths other than the red and IR signal wavelength may be used, such as those from a third wavelength. Alternatively, second order observations of the red and IR signals themselves may provide sufficient information to ignore the artifacts.

Referring again to FIG. 3, in an embodiment, distributions for the plurality of light sources is determined, as indicated at block 34. The distribution of one of the plurality of light sources, such as the third source, can be deconvolved from the distributions of the other light sources, i.e., the red and IR signals, as indicated at block 36, to generate clean distributions. The clean distributions may then be used to compute physiological parameters, as indicated at block 38. For example, the clean red and IR signals may be used to compute the ratrat.

The technique illustrated in FIG. 3 may be advantageous in several aspects. For example, as a saturation signal changes very slowly compared to sampling rate, signal reconstruction provides much more information than needed. Noise deconvolution, however, is not a signal reconstruction technique, as it does not attempt to find the underlying signal $t_k$ or the true IR and red signals. It is, however, an easier problem to solve than reconstruction, and its solution would be implied by a good reconstruction algorithm. Furthermore, it occurs in probability space instead of frequency space. The following provides a theoretical basis for the present techniques.

A Convolution of Sequences

In an embodiment, a bi-infinite sequence is an indexed collection of numbers: ..., g-3, g-2, g-1, g0, g1, g2, ... Such a sequence can be written like a vector, e.g., g. The sequences considered herein have compact support, meaning that only a finite number of nonzero elements are present. Thus, the only functional difference between the sequences considered herein and vectors are that the sequences can have variable length, and indexing matters.

Given two such sequences, f, g, their convolution is defined as:

$$H = f * g \Rightarrow h_i = \sum_j f_j g_{i-j}. \quad (7)$$

When f and g have compact support, so does f*g. Additionally, convolutions on sequences have associative and commutative properties, such that f*g=g*f and (f*g) *h=f*(g*h). Moreover, the summing of two random variables is equivalent to convolving their distribution functions. For example, suppose X and Y are discrete-valued random variables, and that x and y are associated discrete probability density functions. This means that there is an atomic unit of measurement, $\Delta v$ such that $x_i = Pr\{X = i\Delta v\}$, and $y_i = Pr\{Y = i\Delta v\}$. Then the discrete probability density function of Z=X+Y is x*y, or z=x*y.

A Density Estimator

In an embodiment, if G is a finite set of real numbers, the density estimator, H(G) is the bi-infinite sequence h, whose $i^{th}$ element, $h_i$ is the number of elements of G which are in the $i^{th}$ bin. The bins are implicitly understood. Generally, the $i^{th}$ bin is defined as [$i\Delta x$, (I+1)$\Delta x$), so that each bin is of equal width, where $\Delta x$ is implicitly understood. Because G is finite, h=H(G) has compact support.

The normalized $\tilde{H}(G)$, is the sequence $\tilde{h}$ defined as:

$$\tilde{h}_i = h_i \Big/ \sum_j h_i, \quad (8)$$

where h=H(G). That is $\tilde{H}(G)$ is a scaled version H(G) which sums to 1. If G represents a number of independent draws from a random variable, then $\tilde{H}(G)$ gives an estimate of the probability distribution function of the random variable, subject to the width of the bins and the number of draws.

Figure 4:
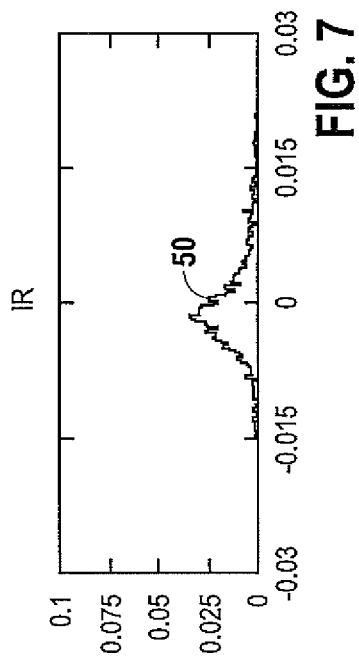
FIG. 4 illustrates a clean density estimator for an IR signal in accordance with an embodiment.
Figure 5:
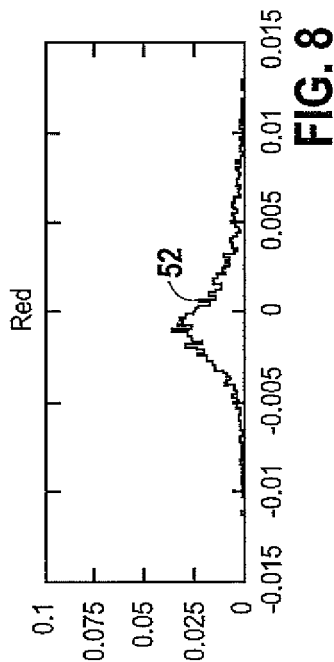
FIG. 5 illustrates a clean density estimator for a red signal in accordance with an embodiment.
Figure 6:
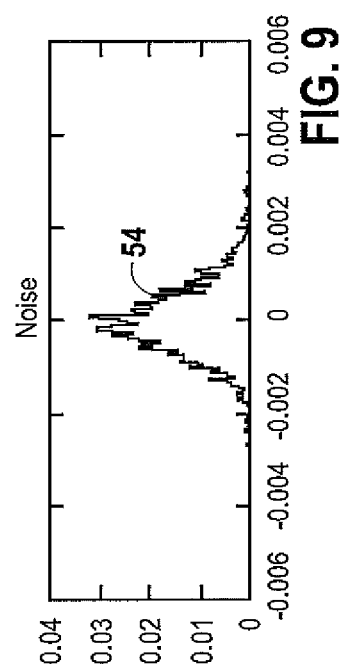
FIG. 6 illustrates a clean density estimator for a noise signal in accordance with an embodiment.
Figure 7:
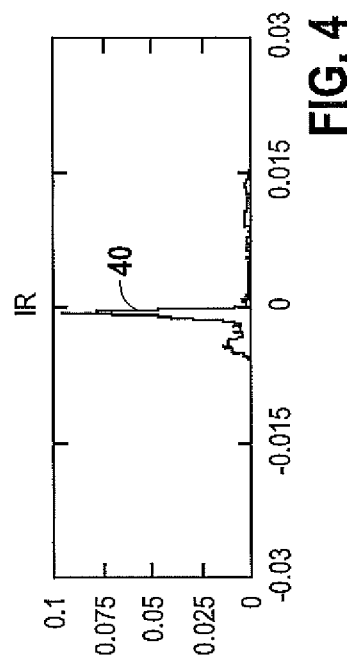
FIG. 7 illustrates a noisy density estimator for an IR signal in accordance with an embodiment.
Figure 8:
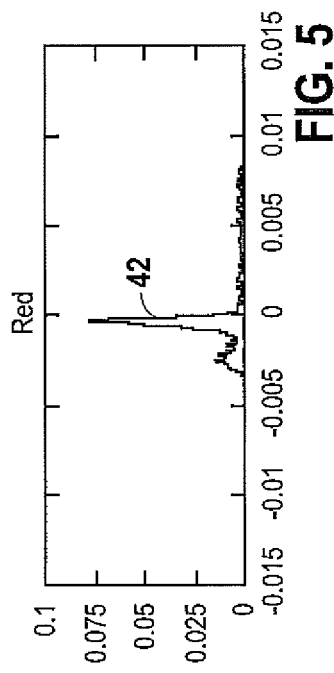
FIG. 8 illustrates a noisy density estimator for a red signal in accordance with an embodiment.
Figure 9:
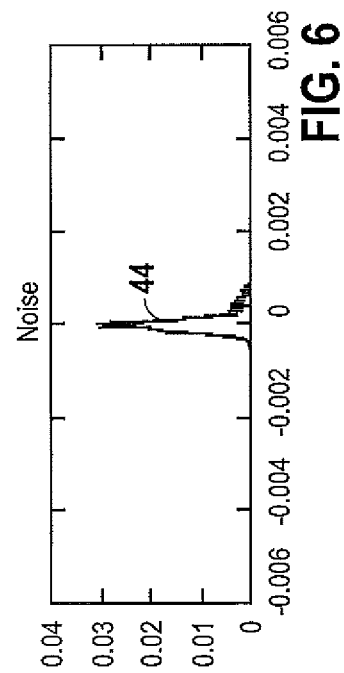
FIG. 9 illustrates a noisy density estimator for a noise signal in accordance with an embodiment.

Accordingly, let $V_{1:l}$ and $U_{1:l}$ denote the collections of red and IR optical density observations, respectively, from timestep 1 to l. The normalized density estimators $\tilde{H}(V_{1:l})$ and $\tilde{H}(U_{1:l})$ approximate the probability density functions of the red and IR signals as random variables. This means that if an integer k is selected uniformly at random from 1, 2, 3, ..., l, and $u_k$ and $v_k$ are then viewed, the probability of those random variables would be described by the normalized density estimators $\tilde{H}(V_{1:l})$ and $\tilde{H}(U_{1:l})$. Such normalized density estimators are shown in FIGS. 4, 5, 6, 7, 8 and 9. Specifically, FIGS. 4, 5 and 6 illustrate noiseless collects of a normalized density estimator 40 of the IR optical density, a normalized density estimator 42 of the red optical density, and a normalized density estimator 44 of a noise signal $n_k$ optical density, respectively. FIGS. 7, 8 and 9 illustrate noisy collects of a normalized density estimator 50 of the IR optical density, a normalized density estimator 52 of the red optical density and a normalized density estimator 54 of the noise signal $n_k$, respectively.

According to various embodiments, each density estimator in FIGS. 4, 5, 6, 7, 8 and 9 represents 3200 data points sampled at 53 Hz. The density estimator for the noiseless and noisy collects, however, do not resemble each other, and the density estimators 44 and 56 have larger support by about half an order of magnitude. The density estimators 40, 42, 44, 50, 52, and 54 in all have the same scale in the value axis (y-axis) to emphasize the spread caused by artifact. However, as can be seen, the IR density estimator 40 and the red density estimator 42 have the same shape, as do the IR density estimator 50 and the red density estimator 52, subject to scaling differences in the x-axis. This is expected, as the saturation is not expected to change much during sampling. Additionally, the scaling difference between the value red and IR plots approximates the ratrat, as it is indicative of the ratio between the red optical density and IR optical density signals.

Additionally, each of the density estimators 40, 42 and 44 have a well defined peak. Alternatively, the density estimators 50, 52 and 54 are significantly more distributed due to the noise. Because of the distribution it is difficult to see similarities between the density estimators 50, 52 and 54 of the noisy collects and the density estimators 40, 42 and 44 of the noiseless collects. As such, the density estimators for the clean and noisy collects do not resemble each other and the density estimators for the noisy collects have larger support by about a half an order of magnitude. Therefore, the removal of the noise from the signals during noisy collects may help in achieving a more accurate estimation of physiological parameters.

For additional information regarding scale functions and density estimators, the book *Introduction to Robust Estimation and Hypothesis Testing*, second edition, R and R. Wilcox, Elsevier, Amsterdam (2005), may be referenced and is incorporated herein in its entirety and for all purposes.

The Algorithm and Calibration

In an embodiment, the proposed algorithm for estimating physiological parameters by deconvolving artifacts relies on the third channel, which can be an independent wavelength or a number of wavelengths combined together, and has been denoted $n_k$. Observations of the noise signal $n_k$ allow for estimation of random processes that generate $\{\epsilon_k\}_k$ and $\{\zeta_k\}_k$. Specifically, the distributions of the noise signal $n_k$ can be deconvolved from the normalized density estimators of observed red and IR signals, afterwhich, the scale parameters can be accurately estimated.

The simplest way to generate distributions of $\epsilon_k$ and $\zeta_k$ is to apply two functions to the collection values $N_{1:l}$ and take the normalized density estimator. Let the functions be $\emptyset_r$ and $\emptyset_i$. The simplest model for functions $\emptyset_r$ and $\emptyset_i$ are of two linear functions such as:

$$\emptyset_r(x) = c_r x, \text{ and} \quad (9)$$

$$\emptyset_i(x) = c_i x, \quad (10)$$

where the two constants $c_r$ and $c_i$ are to be determined. The noise signal $n_k$ of the third channel corresponds directly to the artifact parts $\epsilon_k$ and $\zeta_k$, but needs to be translated into the right units. The third channel is not purely corrupting noise, rather, it is only related is some way to the corrupting noise. For example, if the third signal is an optical signal, and the corrupting noise comes from decoupling of the optical sensor (e.g., the oximeter sensor moves around on the finger), this decoupling will affect all three signals similarly but not identically, as it may depend on several factors, such as, the efficiencies of the detectors, their apertures, etc., for example. In this case, to translate the signal of the third wavelength into something equivalent to the corrupting noise, one may have to perform a scale transform(s), or make a nonlinear transform of some kind (listed in equation (23)). Alternatively, if the third signal is non-optical (such as a piezo electric sensor, or a magnetic induction sensor, etc. for example), the signal may be considered in terms of standard units such as pounds per square-inch, ohms, etch, which may be converted or translated into optical density unit equivalents in the red and IR wavelengths.

In an embodiment, a noise deconvolution saturation estimator may operate as shown in Algorithm 1 below. Note that since the values are grouped into density estimators before being deconvolved, there is some inherent loss of accuracy. Thus, accuracy of the method is affected by the bin-width. Moreover, the assumption that the density estimator represents the probability distribution function only works for a large sample size, such as, more than 100 samples, for example. As such, a meaningful result at rates lower than 1 Hz may be difficult to achieve.

---

Algorithm 1 - Saturation estimator algorithm
with artifact deconvolved.

---

Input: Sequences of red, IR, and noise signals, the posting rate
Output: the estimated saturation
DECONVOLVESAT ($v_{1:k}$, $u_{1:k}$, $n_{1:k}$, prate)
(1)    Let lo ← 1, hi ← prate
(2)    while lo < k
(3)        let hi ← min (k, hi).
(4)        Let V ← $\tilde{H}$ ($v_{lo:hi}$), U ← $\tilde{H}$ ($u_{lo:hi}$), Nr ← $\tilde{H}$ ($\emptyset_r(n_{lo:hi})$), $N_i$ ← $\tilde{H}$ ($\emptyset_i(n_{lo:hi})$)
(5)        Deconvolve: R ← DECON (V, $N_r$), I ← DECON (U, $N_i$).
(6)        Compute the appropriate scale parameters of R and I. Let $\hat{s}_{lo:hi}$ be the ratio of the scale parameters.
(7)        let lo ← hi + 1.
(8)        let hi ← hi + prate.
(9)    return $\hat{s}_{1:k}$

---

The actual deconvolution may be performed by applying a least squares framework. A least squares framework is represented in Algorithm 2 and discussed in greater detail below.

---

Algorithm 2 - Least Squares Nonnegative Deconvolver.

---

DECON (f, h)
(1)    Formulate the toeplitz matrix A associated with f.
(2)    Find vector g with nonnegative elements such that $(Ag - f)^T (Ag - f)$ is minimized.
(3)    return g.

---

Deconvolution

Given the sequences f and h, finding the sequence g such that h=f*g presents some complications. Specifically:
1. There may not be a sequence g that solves this problem and which has compact support. That is, the solution has an infinite number of nonzero elements. This solution is found by using the Fourier Transform and dividing but is typically 'unstable' because the elements become increasingly large in magnitude as the index diverges.
2. By switching to a least-squares framework and restricting the search to compact sequences of a bounded number of nonzero elements, the solution may have negative elements, which cannot currently be interpreted as (scaled) density estimator values.

The least squares problem may be formulated as follows: find g with at most n+1 nonzero elements such that $\|h-f*g\|_2$ is minimized. Let I be the lowest index of a nonzero element of f, I+m be the highest index of a nonzero element of f, and j be the lowest index of g.

A matrix A may be written:

$$f*g = \begin{bmatrix} fi & 0 & 0 & \cdots & 0 \\ fi+1 & fi & 0 & \cdots & 0 \\ fi+2 & fi+1 & fi & \cdots & 0 \\ \cdots & \cdots & \cdots & \cdots & \cdots \\ fi+n & fi+n-1 & fi+n-2 & \cdots & fi \\ \cdots & \cdots & \cdots & \cdots & \cdots \\ fi+m & fi+m-1 & fi+m-2 & \cdots & fi+m-n \\ 0 & fi+m & fi+m-1 & \cdots & fi+m-n+1 \\ 0 & 0 & fi+m & \cdots & fi+m-n+2 \\ \cdots & \cdots & \cdots & \cdots & \cdots \\ 0 & 0 & 0 & \cdots & fi+m \end{bmatrix} \begin{bmatrix} gj \\ gj+1 \\ gj+2 \\ \cdots \\ gj+n \end{bmatrix} \quad (12)$$

$$= Ag,$$

where the matrix A is Toeplitz matrix. The least-squares formulation, without the non-negativity constraint in g, is described by the normal equation: $A^T A g = A^T h$. Because of the special structure of A, we have:

$$A^T A = \begin{bmatrix} \gamma 0 & \gamma 1 & \gamma 2 & \cdots & \gamma n \\ \gamma 1 & \gamma 0 & \gamma 1 & \cdots & \gamma n-1 \\ \gamma 2 & \gamma 1 & \gamma 0 & \cdots & \gamma n-2 \\ \cdots & \cdots & \cdots & \cdots & \cdots \\ \gamma n & \gamma n-1 & \gamma n-2 & \cdots & \gamma 0 \end{bmatrix}, \quad (13)$$

where $\gamma_i$ is the sample autocovariance of the sequence. (An actual sample autocovariance typically involves a subtraction of the first moment which is ignored here.) The matrix $A^TA$ is symmetric, positive, definite, and Toeplitz, which makes the unconstrained least squares problem amenable to specialized techniques such as the Levinson-Durbin algorithm or the Anderson-Bitmead algorithm, which speed up the computation considerably from the usual $O(n^3)$ runtimes for Gaussian Elimination [1]. It is not clear if these algorithms can be altered for the constrained system, however. It may be easier to adapt the scale estimator to the case of negative density estimator values.

A constrained least squares deconvolution problem can be formulated as a bounded quadratic programming problem:

$$g \in R_{n+1}^{min}, g \geq 0 \|Ag - h\|_2^2. \tag{14}$$

The objective function is $$\|Ag - h\|_2^2 = g^T A^T A g - 2h^T A g + h^T h,$$

which is quadratic in g. As implemented for a calibration study, the deconvolution routine formulates this problem and delegates the solution to a quadratic programming algorithm, which is computationally expensive, even when seeded with the unconstrained optimal solution as an initial guess.

Calibration

Figure 10:
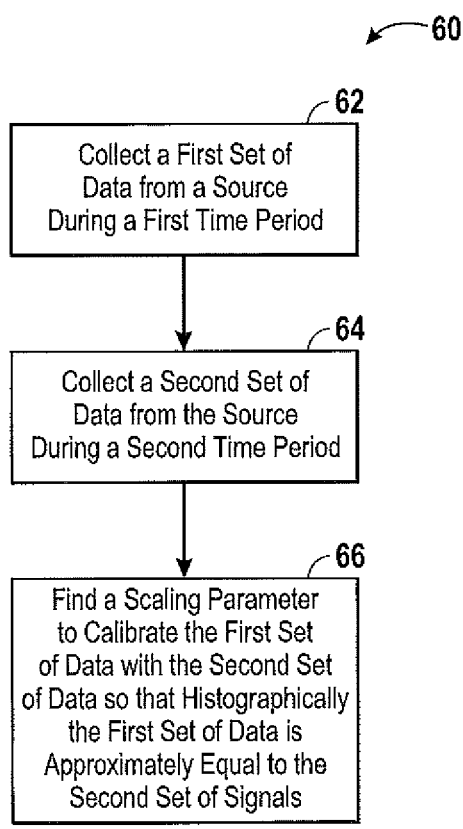
FIG. 10 is a flow chart illustrating a technique for distribution calibration in accordance with an embodiment.

In an embodiment, the functions $Ø_r$ and $Ø_i$ of equations (9) and (10), and Algorithm 1 are found through a calibration process. The calibration may be difficult, however, as the noise channel is not identically zero during the "noiseless" collects, as illustrated by the density estimator 44 in FIG. 6. To account for this, in calibrating for $Ø_i$, two time intervals for the same subject are taken and then calibrated so that the sampling from the two time intervals are equivalent. FIG. 10 illustrates a flow chart representation of a technique 60 for calibration in accordance with an exemplary embodiment of the present invention.

In an embodiment, the technique 60 begins by collecting data during a first time period from a single source, as indicated in block 62. A second set of data is collect from the source during a second time period, as indicated at block 64. For example, two samples for the IR or red signal may be taken. For convenience, call them 1:n and n+1:m. The time steps 1:n may be considered "clean," and n+1:m may be considered "noisy," although there need not be such a distinction. The normalized density estimators then are:

$$h_1 = \hat{H}(U_{1:n}), \tag{15}$$

$$f_1 = \hat{H}(Ø_i(N_{1:n})), \tag{16}$$

$$h_1 = \hat{H}(U_{n+1:m}), \tag{17}$$

$$f_1 = \hat{H}(Ø_i(N_{n+1:m})), \tag{18}$$

where the function $Ø_i$ is a candidate function. Assuming that the subject's cardiac characteristics are the same for the two collects, the density estimators may be presented as:

$$h_1 = f_1 * g, \tag{19}$$

$$h_2 = f_2 * g, \tag{20}$$

where g is the normalized density estimator representing the discrete probability density function of the cardiac signal. Referring again to FIG. 10, a scaling parameter is found to calibrate the first and second data so that they are approximately equal, or so that they exhibit approximately equal distributions, as indicated in block 66. Specifically, manipulation of the equations (19) and (20) using commutative and associative properties produces:

$$f_2 * h_1 = f_2 * f_1 * g, \tag{21}$$

$$f_1 * h_2 = f_1 * f_2 * g = f_2 * f_1 * g, \tag{22}$$

Thus, calibration for the data sets consists of finding $Ø_i$ such that $$f_2 * h_1 = f_1 * h_2 \tag{23}$$

If $Ø_i$ is parameterized by a single parameter, for example, if $Ø_i$ is linear, then finding the optimal parameter can be easily achieved with a brute-force search, since the range of the parameter can be bounded in advance by inspection. That is, for an particular signal's optical density, the scale of noise should not be larger than the observed signals, but should be larger than zero.

Figure 11:
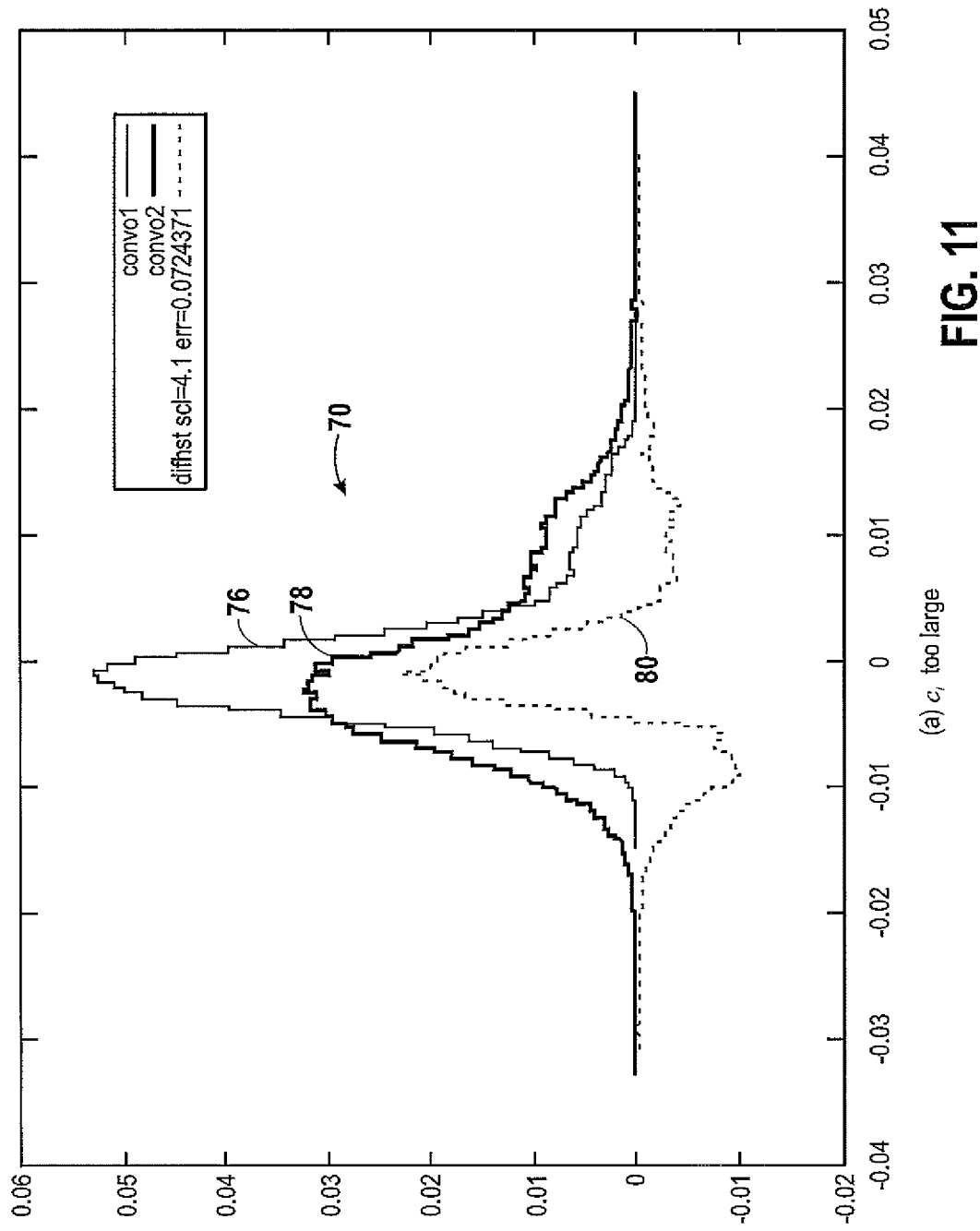
FIG. 11 illustrates a calibration of a linear transform wherein a linear parameter is too large, according to an embodiment.
Figure 12:
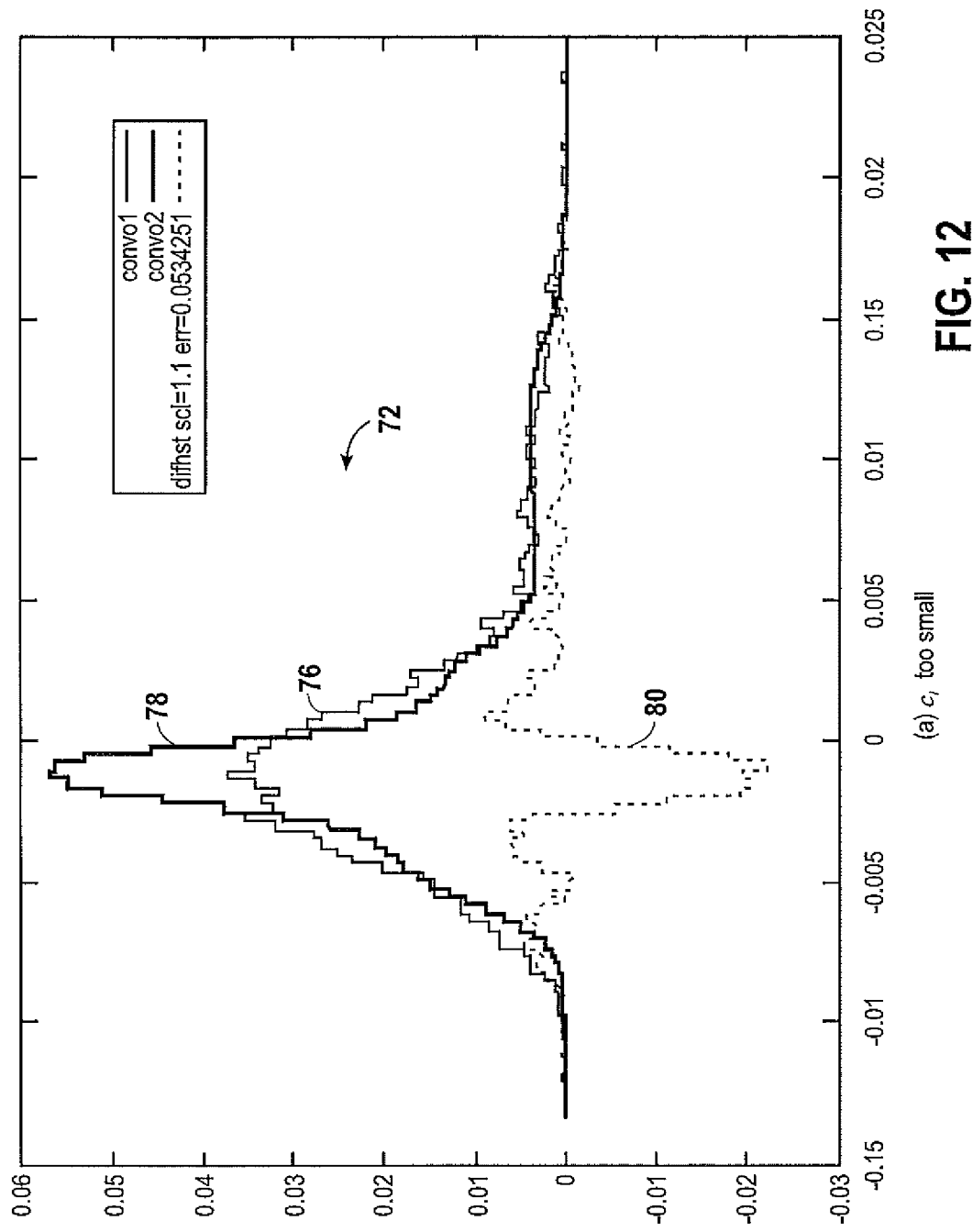
FIG. 12 illustrates a calibration of a linear transform wherein the linear parameter is too small, according to an embodiment.
Figure 13:
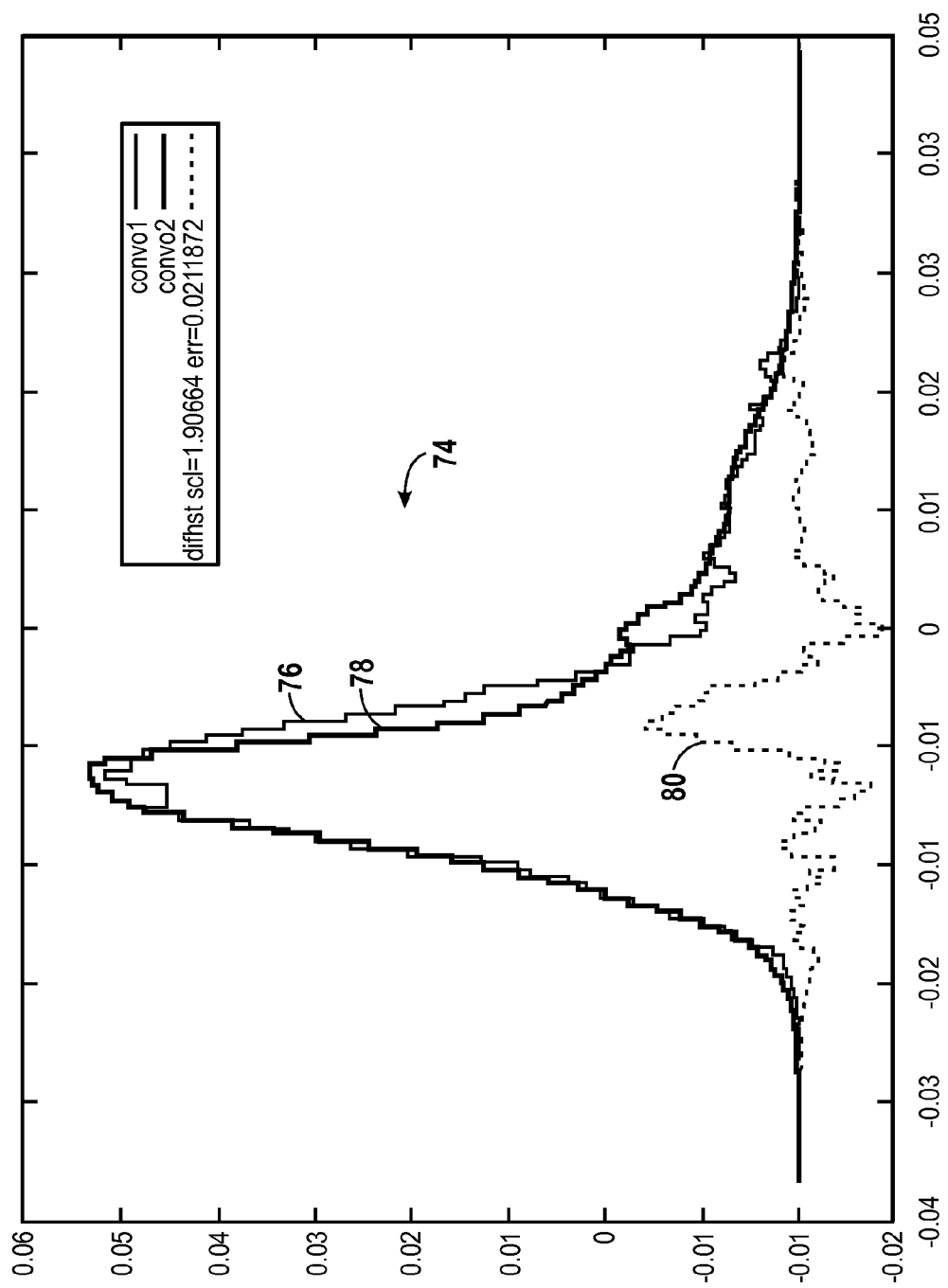
FIG. 13 illustrates a calibration of a linear transform wherein the linear parameter is nearly optimal, in accordance with an embodiment.

In an embodiment, the selection of an appropriate scaling parameter $c_i$ is graphically illustrated in plots 70, 72, and 74 of FIGS. 11, 12 and 13, respectively, which show three choices of the parameter for a linear transform $Ø_i$. In each of the FIGS. 11, 12 and 13, a first plot line 76 represents a first observed IR distribution which may be described as an underlying IR distribution convoluted with a noise distribution. A second plot line 78 represents a second observed IR distribution representing an underlying IR distribution convoluted with a noise distribution. A third plot line 80 represents a scaled noise distribution. In FIG. 11, the plot 70 shows the third plot line 80 as indicating that the scaling parameter of the noise distribution is too large, as the scaling factor does not allow for equation 23 to be true. This is shown by the first plot line 76 having a more concentrated or less spread distribution the plot line 78.

In FIG. 12, the plot 72 shows the third plot line 80 as being inverted, indicating that the scaling parameter for the noise signal is too small. This is illustrated further by the plot line 76 having a wider distribution than the plot line 78. In FIG. 13, the plot 74 shows the third plot line 80 as being nearly optimal, as the plot lines 76 and 78 have nearly the same distribution and, thus, the two sides of equation 23 are approximately equivalent. The calibration using a linear transform was attempted and the experiment is discussed in detail below.

Linear Calibration Experiment

The basic experiment includes:
1. Gathering red and noise signals over two separate periods;
2. Compute the density estimators of the red signal over both periods) call them $f_1$ and $f_2$;
3. Use the translation to translate the noise signal in to the red equivalent and construct density estimators $h_1$ and $h_2$; and
4. As indicated in equation (23), and because of the commutative and associative properties of convolution, $f_2 * h_1 = f_1 * h_1$ should be met regardless of the presence of strong noise if the cardiac signals are relatively constant over the two time periods. This equation (and the same equation for the IR signal and the translation of the third signal into IR equivalent) is satisfied when the technique is properly estimating the distribution of noise in the distributed signals.

Consider the calibration of two different parts of the same collect data. That is, as above, consider the three time intervals 1:n, n+1:n, and m+1:l. In laboratory experiments, the first interval was clean, while the other two intervals had different kinds of artifacting (scratching versus tapping). Using the same language as above, a linear calibration was attempted to get $$f_2 * h_1 = f_1 * h_2, \quad (24)$$

then another calibration was attempted to get $$f_3 * h_1 = f_1 * h_3. \quad (25)$$

The same calibration was expected, but the results were different by a factor of two. The results are tabulated in Table 1. Specifically, Table 1 shows

| Noise Interval | $c_i$ | $c_r$ |
|---|---|---|
| Interval 2 | 1.63590393 | 1.33100586 |
| Interval 3 | 4.08316895 | 2.53460938 |

The scaling factors in the Red and IR form a devonvolution calibration on two different noise intervals. The parameters were found with a Nelder Mead brute-force search to minimize the $L_\infty$ norm. The density estimators had 80 bins.

Theoretically, any proposed choice of transforms $\emptyset_i$ and $\emptyset_r$ should produce the same results when calibrated multiple times under the following procedure: Randomly partition a collect into three equal-sized sets, numbered 1, 2, 3, and then calibrate the functions to get $f_2 * h_1 = f_1 * h_2$.

There are a number of reasons the calibration may have been off by the factor of two. For example:
The additive model of equation (4) may not apply. This may have profound effects on any attempt at noise-deconvolved saturation estimation.
The linear model for $\emptyset_i$ and $\emptyset_r$ is not appropriate. This may be corrected by finding an appropriate calibration model for the $\emptyset_i$ and $\emptyset_i$.
The noise channel used in the experiments was not appropriate.

Because of the inherent non-linearity of the calibration problem, the transforms $\emptyset_i$ and $\emptyset_r$ may be kept simple, e.g., parametrized by a single parameter each, Any of the following proposed transforms might be applicable, although there is no theoretical reason for proposing any of them other than simplicity:

$$\emptyset_1(x) = cx^3, \emptyset_2(x) = cx^{1/3}, \quad (26)$$

$$\emptyset_3(x) = c \arctan x, \emptyset_4(x) = c \frac{e^x - 1}{e^x + 1}.$$

As far as other noise channels, the obvious suspects are: another optical channel at a different wavelength or combination of wavelengths; a Cauchy distribution (or a Gaussian) whose width is determined by the second moment of the signal of an optical channel or by the width of the biggest peak in the Fourier Transform of the optical signals; the residual of a linear least squares fit or other fit.

While the disclosure may be conducive to various modifications and alternative forms, embodiments have been shown by way of example in the drawings and have been described in detail herein. However, it should be understood that the disclosure is not intended to be limited to the particular forms disclosed. Rather, the disclosure is to cover all modifications, equivalents, and alternatives falling within the spirit and scope of the invention as defined by the following appended claims.

The invention claimed is:

1. A method for non-invasively estimating a physiological parameter comprising:
   detecting light over a period of time from a plurality of light sources comprising at least three light sources;
   generating respective distributions for the detected light of each of the plurality of light sources for the period of time;
   deconvolving the distribution for the detected light of one of the plurality of light sources from each of the other distributions for the detected light from the other plurality of light sources to produce clean distributions for the period of time; and
   estimating a physiological parameter based at least in part upon the clean distributions;
   wherein deconvolving the distribution for the detected light of one of the plurality of light sources comprises using a least squares algorithm, wherein the least squares algorithm comprises:
   formulating a toeplitz matrix A associated with f; and
   finding a vector g with nonnegative elements such that $(Ag-f)^T(Ag-f)$ is minimized, wherein g and f are bi-infinite sequences.

2. The method of claim 1, wherein the distribution for the detected light of the one of the plurality of light sources is utilized to estimate the distribution of noise artifacts in a detected signal.

3. The method of claim 1, wherein the plurality of light sources comprises a first light source operating in the red region of the electromagnetic spectrum, a second light source operating in the infrared region of the electromagnetic spectrum, and a third light source operating in region of the electromagnetic spectrum that is selected to detect noise.

4. The method of claim 3, wherein the third light source operates in a blue region of the electromagnetic spectrum.

5. The method of claim 3, wherein the third light source operates in a region comprising the wavelengths approximately in the range of 1250 to 1350 nm.

6. The method of claim 1, wherein deconvolving the distribution for the detected light of the one of the plurality of light sources comprises using a least squares algorithm, wherein the least squares algorithm is solved using nonnegative matrix factorization relaxation steps.

7. The method of claim 1, wherein the method further comprises calibrating functions representative of the distribution of a noise signal.

8. The method of claim 7, wherein calibrating functions representative of the distribution of the noise signal comprises:
   collecting a first set of data for each of the plurality light sources;
   collecting a second set of data for each of the plurality of light sources; and
   parameterizing the functions representative of the distribution of the noise signal, wherein parameterizing the functions comprises finding a parameter to produce approximately equal distributions of the first and second sets of data.

9. The method of claim 4, wherein computing physiological parameters comprises determining a scaling difference between distributions of detected light for the red and infrared light sources.

10. The method of claim 1, wherein estimating the physiological parameter comprises estimating a blood oxygen saturation.

11. The method of claim 10, further comprising displaying the blood oxygen saturation on the monitor.

12. The method of claim 1, wherein the three light sources operate at different wavelengths from each other.

13. The method of claim 1, further comprising passing light from the three light sources through blood-perfused tissue, prior to detecting the light.

14. A system for estimating a physiological parameter comprising:
- a sensor comprising:
  - a plurality of light sources; and
  - a detector configured to generate signals based on detected light from the plurality of light sources over a period of time; and
- a monitor coupled to the sensor configured to:
  - generate distribution data based on the detected light for the period of time for each of the plurality of light sources; and
  - deconvolve distribution data for the period of time of one of the plurality of light sources from the distribution data of each of the other plurality of light sources for the period of time, to produce clean distributions;
  - wherein deconvolving the distribution data comprises the monitor using a least squares algorithm, wherein the least squares algorithm comprises:
    - formulating a toeplitz matrix A associated with f; and
    - finding a vector g with nonnegative elements such that $(Ag-f)^T(Ag-f)$ is minimized, wherein q and f are bi-infinite sequences.

15. The system of claim 14, wherein the plurality of light sources comprises three light sources operating at different wavelengths.

16. The system of claim 15, wherein the three light sources comprise:
- a first light source operating in the red region of the electromagnetic spectrum; and
- a second light source operating in the IR region of the electromagnetic spectrum.

17. The system of claim 14, wherein at least one of the plurality of light sources is used to obtain data related to artifacts.

18. The system of claim 17, wherein the monitor is configured to find functions representative of the artifacts through a calibration process, wherein the calibration process comprises parameterization of the functions.

19. The system of claim 14, wherein the monitor is further configured to estimate a physiological parameter based at least in part on the clean distributions.

20. The system of claim 19, wherein the parameter comprises blood oxygen saturation.

21. A method for non-invasively estimating a physiological parameter comprising:
- detecting light over a period of time from a plurality of light sources comprising at least three light sources;
- generating respective distributions for the detected light of each of the plurality of light sources for the period of time;
- calibrating functions representative of a distribution of a noise signal,
- wherein calibrating functions representative of the distribution of the noise signal comprises:
  - collecting a first set of data for each of the plurality light sources;
  - collecting a second set of data for each of the plurality of light sources; and
  - parameterizing the functions representative of the distribution of the noise signal, wherein parameterizing the functions comprises finding a parameter to produce approximately equal distributions of the first and second sets of data;
- deconvolving the distribution for the detected light of one of the plurality of light sources from each of the other distributions for the detected light from the other plurality of light sources to produce clean distributions for the period of time; and
- estimating a physiological parameter based at least in part upon the clean distributions.

22. A system for estimating a physiological parameter comprising:
- a sensor comprising:
  - a plurality of light sources; and
  - a detector configured to generate signals based on detected light from the plurality of light sources over a period of time; and
- a monitor coupled to the sensor configured to:
  - generate distribution data based on the detected light for the period of time for each of the plurality of light sources;
  - calibrate functions representative of a distribution of a noise signal, wherein calibrating functions representative of the distribution of the noise signal comprises:
    - collecting a first set of data for each of the plurality light sources;
    - collecting a second set of data for each of the plurality of light sources; and
    - parameterizing the functions representative of the distribution of the noise signal, wherein parameterizing the functions comprises finding a parameter to produce approximately equal distributions of the first and second sets of data; and
  - deconvolve distribution data for the period of time of one of the plurality of light sources from the distribution data of each of the other plurality of light sources for the period of time, to produce clean distributions.

* * * * *